US008088149B2

(12) United States Patent
White

(10) Patent No.: US 8,088,149 B2
(45) Date of Patent: Jan. 3, 2012

(54) DYNAMIC INTERVERTEBRAL STABILIZATION SYSTEM

(75) Inventor: Patrick White, West Chester, PA (US)

(73) Assignee: Greatbatch Medical S.A., Orvin (CH)

( * ) Notice: Subject to any disclaimer, the term of this patent is extended or adjusted under 35 U.S.C. 154(b) by 440 days.

(21) Appl. No.: 12/297,874

(22) PCT Filed: Apr. 21, 2007

(86) PCT No.: PCT/IB2007/001050
§ 371 (c)(1),
(2), (4) Date: Oct. 21, 2008

(87) PCT Pub. No.: WO2007/122494
PCT Pub. Date: Nov. 1, 2007

(65) Prior Publication Data
US 2009/0281572 A1    Nov. 12, 2009

Related U.S. Application Data

(60) Provisional application No. 60/871,894, filed on Dec. 26, 2006, provisional application No. 60/745,282, filed on Apr. 21, 2006.

(51) Int. Cl.
*A61B 17/70* (2006.01)
(52) U.S. Cl. .................. 606/258; 606/264; 606/275
(58) Field of Classification Search .................. 606/246, 606/254–279; 403/104–108, 118, 196, 197, 403/200
See application file for complete search history.

(56) References Cited

U.S. PATENT DOCUMENTS

| 4,274,401 | A | * | 6/1981 | Miskew | 606/276 |
| 4,641,636 | A | * | 2/1987 | Cotrel | 606/250 |
| 4,946,458 | A | * | 8/1990 | Harms et al. | 606/305 |
| 5,257,994 | A | * | 11/1993 | Lin | 606/272 |
| 5,261,912 | A | * | 11/1993 | Frigg | 606/302 |
| 5,282,863 | A | * | 2/1994 | Burton | 606/254 |
| 5,352,226 | A | * | 10/1994 | Lin | 606/264 |
| 5,382,248 | A | * | 1/1995 | Jacobson et al. | 606/60 |
| 5,476,462 | A | * | 12/1995 | Allard et al. | 606/60 |
| 5,486,174 | A | * | 1/1996 | Fournet-Fayard et al. | 606/261 |
| 5,738,685 | A | * | 4/1998 | Halm et al. | 606/270 |
| 5,938,663 | A | * | 8/1999 | Petreto | 606/278 |
| 5,961,517 | A | * | 10/1999 | Biedermann et al. | 606/86 A |
| 6,117,137 | A | * | 9/2000 | Halm et al. | 606/308 |
| 6,302,410 | B1 | * | 10/2001 | Wentworth et al. | 279/152 |
| 7,083,621 | B2 | * | 8/2006 | Shaolian et al. | 606/86 A |
| 7,678,139 | B2 | * | 3/2010 | Garamszegi et al. | 606/328 |
| 7,766,915 | B2 | * | 8/2010 | Jackson | 606/86 A |
| 2003/0220642 | A1 | * | 11/2003 | Freudiger | 606/61 |
| 2005/0277924 | A1 | * | 12/2005 | Roychowdhury | 606/61 |

FOREIGN PATENT DOCUMENTS

| DE | 196 46 534 A1 | 5/1998 |
| DE | 202 07 848 U 1 | 11/2002 |
| WO | 2006102605 | 9/2006 |

* cited by examiner

*Primary Examiner* — Eduardo C Robert
*Assistant Examiner* — Steven Cotroneo
(74) *Attorney, Agent, or Firm* — Michael F. Scalise

(57) ABSTRACT

A vertebral dynamic stabilization system is used to fix the positional relationship of adjacent vertebrae of the spine. The vertebrae' stabilization system includes at least two pedicle screws(20), with an interconnecting rod (60) disposed therebetween, the pedicle screws each having a threaded shaft (24) to be screwed into a vertebra segment, and a screw head (30) adapted to securely receive the interconnecting rod. The system allows some compression and extension of the vertebrae relative to each other, while still maintaining the overall positional relationship within an appropriate range.

20 Claims, 8 Drawing Sheets

DYNAMIC INTERVERTEBRAL STABILIZATION SYSTEM

CROSS-REFERENCE TO RELATED APPLICATIONS

This application claims priority to U.S. provisional applications, Ser. No. 60/745,282, filed on Apr. 21, 2006, and Ser. No. 60/871,894, filed on Dec. 26, 2006.

FIELD OF THE INVENTION

The present invention is in the field of surgical apparatus used in the treatment of diseases and other abnormal conditions of the spine. More specifically, the present invention relates to orthopedic instrumentation designed for attachment to a portion of the spine to correct a deformity, fracture, or unwanted diseased condition, wherein the means is particularly adapted for positioning vertebrae.

BACKGROUND OF THE INVENTION

The present invention relates to devices used in the surgical arts to fix the positional relationship of vertebrae of the spine, and more particularly to a pedicle screw and rod assembly for this purpose. There are various prior art devices available, which are intended for fixing the positional relationship of the vertebrae of the spine. For example, when attempting to achieve osteosynthesis, the specific fusion of different segments of the spine, one has to provide some type of immobilization. The current different systems typically involve placement of screws into the pedicle region of the vertebrae, which are then connected to each other by use of various sizes of rods, plates, or wires. However, these methods and devices for the fusion of vertebrae are not always appropriate when immobilization to promote fusion is not intended. Therefore, it would be beneficial to have a system with a somewhat flexible means of interconnecting the pedicle screws, and which would allow adjustment of the tension between at least two interconnected pedicle screws where the intent is to avoid fusion of the subject vertebrae.

Spinal degeneration results in the loss of height between the vertebrae. This loss in height usually results in the pinching of a nerve which routes through the vertebrae, hence causing pain. In these cases it is often desirable to restore the spacing between the vertebrae rather than to fuse them. It would be additionally beneficial to have a device that would maintain the surgically restored resting height of the vertebrae, while allowing some flexion, extension and compression of those vertebrae relative to each other. Further, in view of the large number of pedicle screws available in the osteosynthesis field, it would be especially beneficial to have a device that accomplishes these objectives when combined or used with an existing type of osteosynthesis pedicle screw.

SUMMARY OF THE INVENTION

The present invention is a dynamic intervertebral stabilization system for use in the surgical arts to fix the positional relationship of adjacent vertebrae of the spine. The present vertebral stabilization system is "dynamic" in that it allows some motion in the vertebrae while constraining it from over motion. Additionally, it is intended that the present system allow some compression and extension of the vertebrae relative to each other, while still maintaining the overall positional relationship within an appropriate range. The present vertebrae stabilization system comprises at least two pedicle screw assemblies used in combination. In use, two or more pedicle screw assemblies are interconnected in a series by a rod assembly, wherein the "dynamic" feature of the present invention resides, the dynamic feature being that the rod assembly preferably has some elasticity and can provide for some compression and extension over its length and distortion along its axis. The feature allows the vertebrae between which the present system is installed to move relative to each other, while still maintaining the normal overall positional relationship of the vertebrae within an appropriate range.

A pedicle screw assembly of the present system has a threaded shaft and a screw head. The threaded shaft disposed to be screwed into a vertebra segment (typically into the pedicle bone), and the head disposed to connect to the dynamic rod assembly. The screw head has a bottom shank portion, a top surface and a head thickness portion therebetween. The bottom shank portion connects the screw head to the threaded shaft. A receiver portion for receiving and interfacing with a rod assembly is disposed in the top surface of the screw head. The receiver portion is where an anchor portion of the rod assembly is retained. The rod assembly can be of a metallic or a non metallic composition (e.g., a polycarbonate urythane composition).

DETAILED DESCRIPTION

Figure 1:
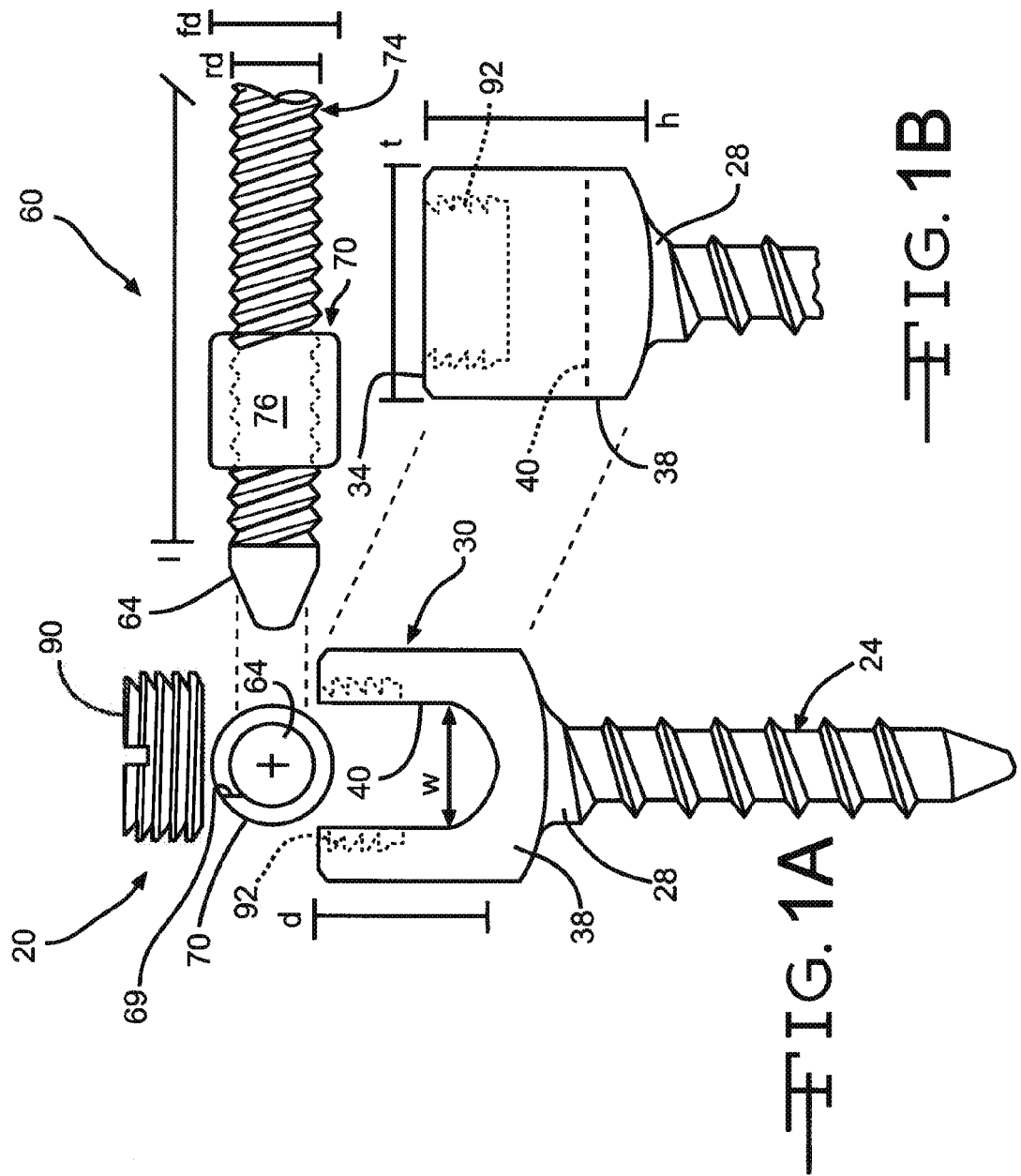
FIG. 1A is a front plan view of a pedicle screw and threaded rod of the present dynamic vertebrae stabilization system, showing front plan and side plan views of the screw head.
FIG. 1B is a side view of the pedicle screw and threaded rod of FIG. 1A.

The present invention is a dynamic vertebrae stabilization system for use in the surgical arts to fix the positional relationship of adjacent vertebrae of the spine. The present intervertebral stabilization system is "dynamic" in that it allows some motion in the vertebrae while constraining the vertebrae from over motion. Additionally, it is intended that the present system allow some compression and extension of the vertebrae relative to each other, while still maintaining the overall positional relationship within an appropriate range.

As illustrated in FIGS. 1A and 1B, the present vertebral stabilization system comprises at least two pedicle screws 20, which are attachable to an interconnecting rod assembly 60. The pedicle screws 20 are intended typically to be anchored into the pedicle bone of adjacent vertebrae (not shown), with the interconnecting rod assembly 60 disposed vertically between them. Also typically, at least two pedicle screw stabilization assemblies are used in a procedure, one stabilization system between the left pedicles of the adjacent vertebrae, and one stabilization system between the right pedicles of the same adjacent vertebrae. The component parts of the present vertebral stabilization system are constructed of materials that are bio-compatible and preferably are additionally MRI-compatible. In fact, the embodiment of FIGS. 1A and 1B is intended to be practiced with an existing pedicle screw, while still accomplishing the benefits of the present dynamic stabilization system.

The pedicle screws 20 have a threaded shaft 24 and a head 30. The threaded shaft 24 is formed to be screwed into a vertebra segment proximate to pedicle bone. Methods and means for inserting the pedicle screw 20 into vertebrae are known in the art. The pedicle screw head 30 has a bottom shank portion 28 by which it is attached to the threaded shaft 24. The screw head 30 also has a top surface 34 at a height h above the bottom shank portion 28 and a head thickness t across the top surface 34 and between the slot faces 38 of the screw head 30. The screw head 30 is adapted to engage a threaded anchor 70 typically proximate the rod end 64 of the interconnecting rod assembly 60.

In a preferred embodiment exemplified in FIG. 1, the screw head 30 is adapted to engage the rod assembly 60 via a rod receiver 40 disposed in the top surface 34 of the screw head 30. In the embodiment illustrated, the rod receiver 40 is a U-slot 40 adapted to receive and retain the anchor 70 of the rod assembly 60. The U-slot 40 is an opening between the slot faces 38 and communicates with the top surface 34 of the screw head 30. Typically, a rod end 64 projects through the U-slot 40. The U-slot 40 has a width w, a depth d and a slot thickness t. The slot thickness t corresponds to the head thickness t of the top surface 34. The depth d is the distance the U-slot 40 extends from the top surface 34 toward the bottom shank portion 28 of the screw head 30.

The interconnecting rod assembly 60 has a connecting rod 74 with multifaceted surface portions which are threaded portions 75 and first and second rod ends 64, a rod diameter rd and a rod length l. The threaded rod 74 has the feature of being somewhat elastic, in that it is capable of being stretched, compressed and flexed over its length l along its axis 71. In a preferred embodiment, a threaded rod 74 having the intended features is made of a polycarbonate urethane composition, and has a rod diameter rd of about 4.0 mm. An advantage of the polycarbonate urethane threaded rod 74 is that this material acts as a good dampener to the motion along its length, but can be rigidly attached to the pedicle screws 20. In the preferred embodiment illustrated, the rod assembly 60 has a rigid anchor 70 that is a threaded cylinder 76 screwed onto the threaded rod 74 from a rod end 64. The anchor 70, regardless of its configuration, which may be of just about any polygonal or cylindrical form, has a cross-sectional dimension fd that allows the anchor 70 to be received into the width w of the U-slot 40. The width w of the slot 40 of a typical existing pedicle screw is about 5.5 mm to 6.0 mm. Therefore, the cross-sectional dimension fd of the anchor 70 is selected to closely approach the width w of the slot 40 of the pedicle screw 20 being used with the present system.

Interconnection between the screw head 30 and the rod assembly 60 is accomplished by the threaded rod 74 being receivable along a portion of its length l into the width w of the U-slot 40 to a depth exceeding the rod diameter rd. With the threaded rod 74 received in the U-slot 40, the anchor 70 is fixable along the length of the threaded rod 74 by screwing a set screw 90 into a set screw receiver 92 of the pedicle screw 20, and tightening the set screw 90 against the anchor 70. In the preferred embodiment shown, tightening the set screw 90 against the anchor 70 is provided with a two stage anchor setting mechanism. In The first stage, the set screw 90 is tightened sufficiently to only fix the anchor 70 in the receiver U-slot 40. At this stage the intervertebral rod 74 is still rotatable within the anchor 70, but the anchor 70 cannot move relatively to the screw head 38. The tension on the intervertebral rod 74 interconnecting two similarly captured/fixed pedicle screw anchors 70 can be adjusted by rotating the threaded rod 74. Subsequent further tightening of the set screw 92 compresses the anchor 70 against the threaded rod 74 like a swage fitting to additionally fix the positional relationship of the anchor and the threaded rod 74. Optionally, the anchor 70 can have a through-slot 69 going from its outside surface to its inside surface, the through-slot 69 providing compression or crush space to facilitate compression of the anchor 70.

The threaded set screw 90 is screwed into the complementary-threaded receiver 92 in the top surface 34 of the screw head 30. The threaded set/cap screw 90 can function to hold the anchor 70 fixed in place in the pedicle screw 20 while the length of the rod assembly 60 is being adjusted to obtain the desired distance between the two pedicle screws 20 of the system. Once the distance relationship is appropriately set, the set screws 90 can be further tightened to fully set the anchor 70 to the threaded rod 74 and prevent its inadvertent rotation and to prevent any slippage or loosening of the rod 74 that might otherwise occur. The set screw cap 90 illustrated is configured as a slotted set screw, but other configurations of the retainer cap 90 suitable for practice in the present invention are known to and selectable by one of ordinary skill in the art.

Figure 2:
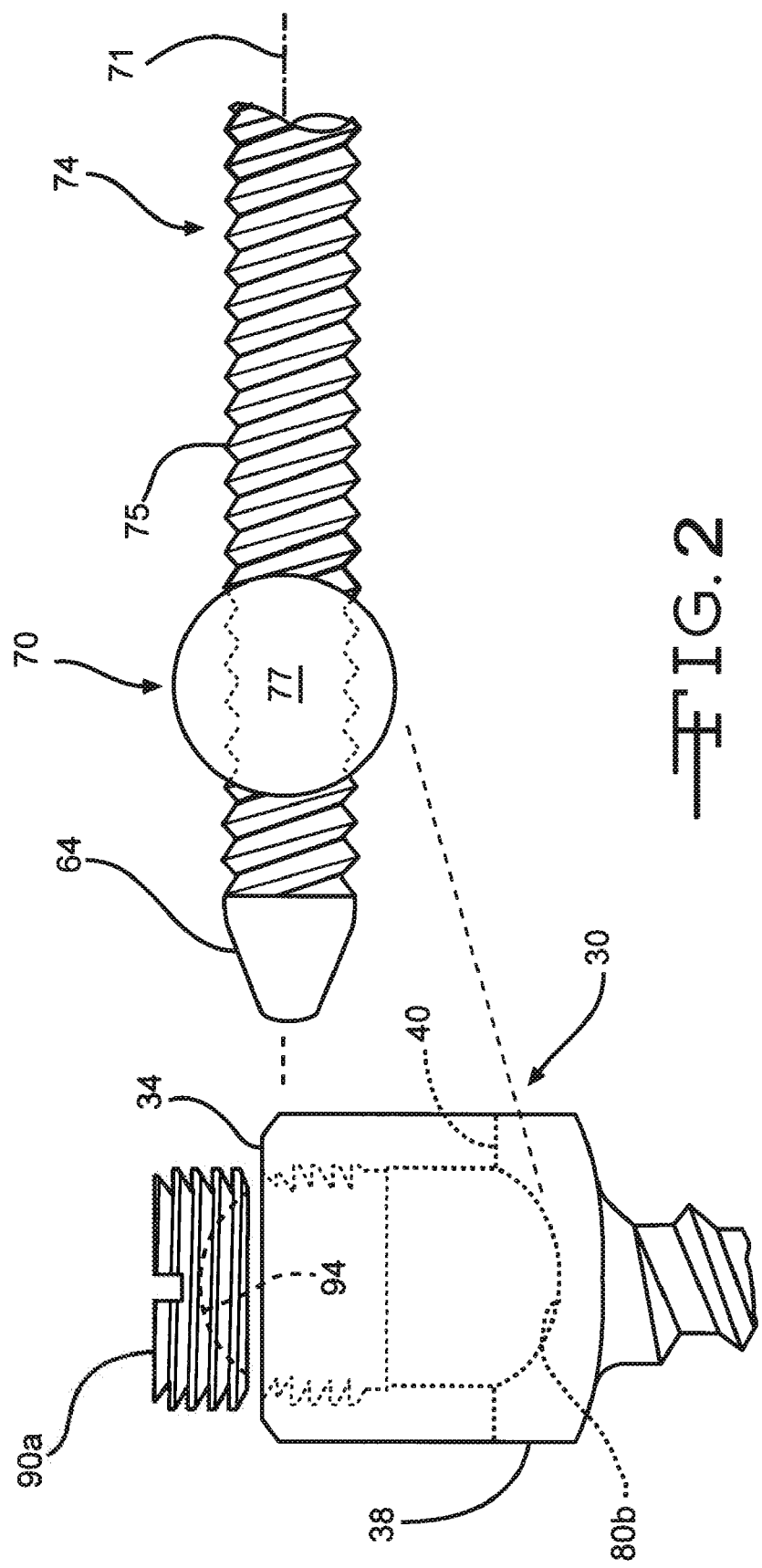
FIG. 2 is a partially disassembled side plan view of the head of a pedicle screw of the present invention showing an alternative embodiment of the head for engaging a ball fastener and threaded rod combination.

Other configurations of the screw head 30 and anchor 70 combination are also anticipated, and are selectable by the ordinary skilled artisan for practice in the present invention. For example, in FIG. 2, the anchor 70 comprises a spherical/ball threaded fastener 77, which is received in a complementary detent recess 80b integral with the U-slot 40 of the screw head 30, i.e., the detent recess 80b is completely within the screw head 30. In this embodiment the set screw cap 90a has a concave lower face 94 that is complementary to the ball fastener 77, to closely receive the ball fastener 77 when the set screw 90a is screwed into place.

Figure 3:
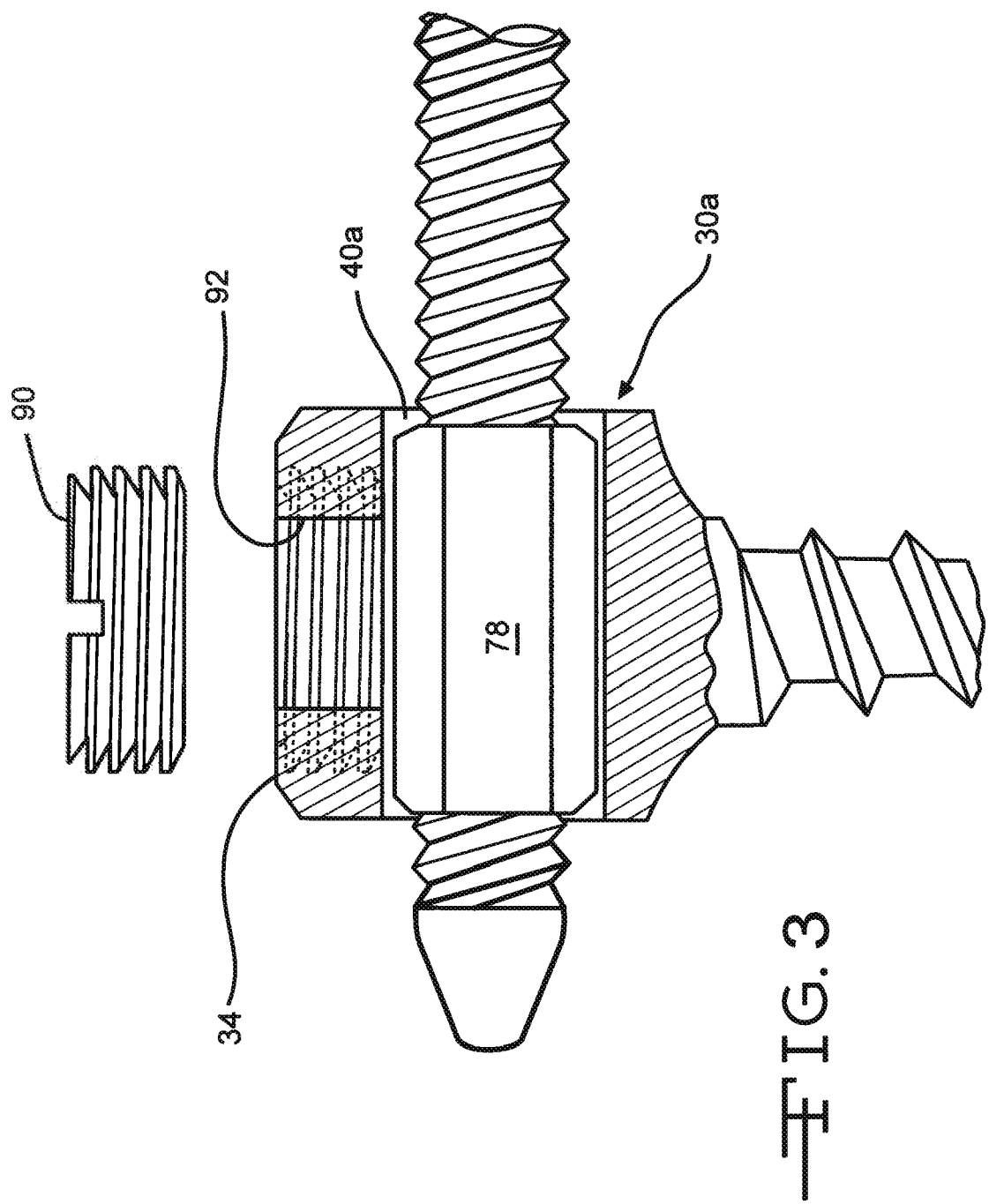
FIG. 3 is a partial cross-sectional side view of the head of a pedicle screw of the present invention showing an alternative embodiment wherein the anchor fastener is a hex nut engaging threaded rod. The hex fastener is fixed in place between the bottom of the U-slot and the set screw/cap.

FIG. 3 illustrates an example of a further alternative embodiment of the screw head 30a, and how it can interconnect with the rod assembly 60. In the embodiment exemplified in FIG. 3, the screw head 30a has a rod receiver passage 40a such as a hexagonally shaped passage rather than a U-slot rod receiver. Pedicle screws with rod receiver passages are known in the art. The rod receiver passage 40a communicates with the set screw receiver 92, which allows the set screw 90 to encroach into the rod receiver passage 40a. The anchor 70 is a threaded hex-fastener 78 that is set against the bottom of the rod receiver passage 40a proximate to the bottom shank 28 of the pedicle screw 20. Setting the threaded hex-fastener 78 against the bottom of the rod receiver passage 40a is accomplished as disclosed above via the action of tightening the set screw 90.

Figure 4:
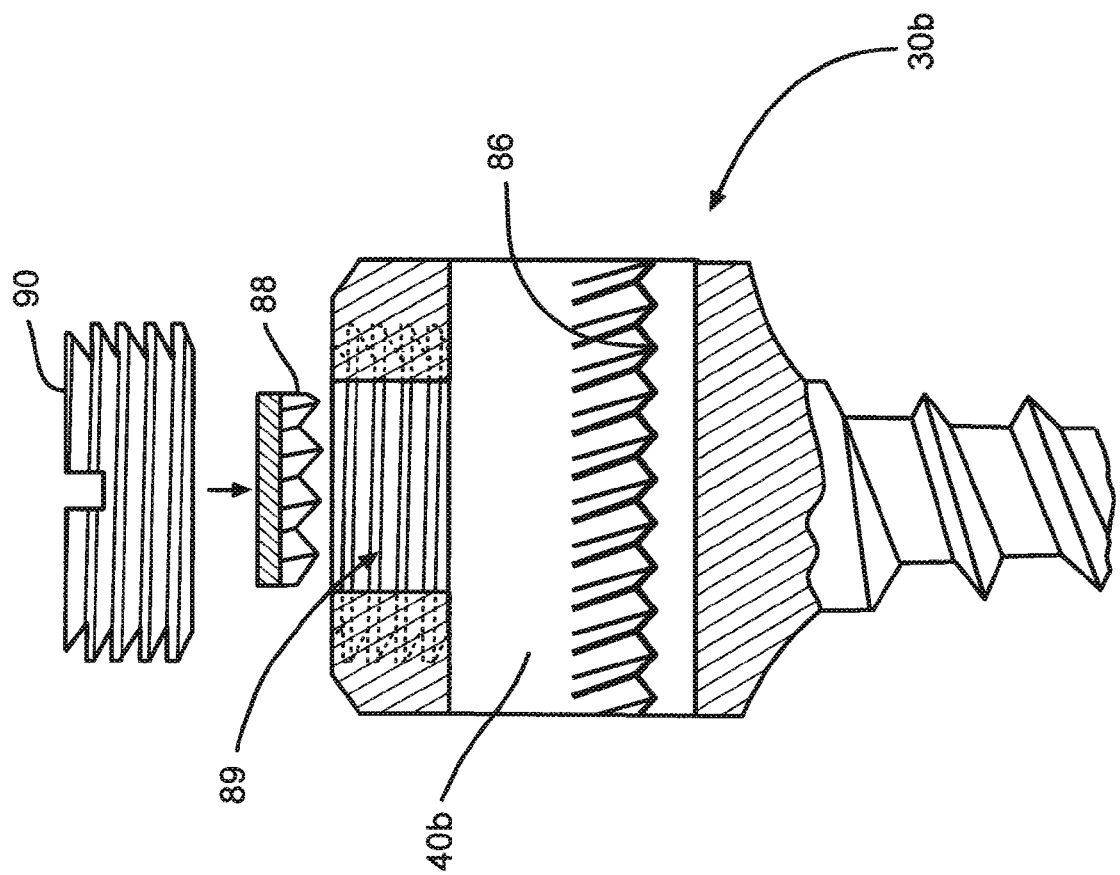
FIG. 4 is a partial cross-sectional side view of the head of a pedicle screw of the present invention showing an alternative embodiment wherein a threaded wedge is used to fix the threaded cylinder in place in the screw head of the pedicle screw.

FIG. 4 illustrates an example of a further alternative embodiment of the pedicle screw 20 having a screw head 30b for receiving the threaded connecting rod 74. The screw head 30b includes threads 86 disposed at a base portion of the U-slotted receiver 40b and a matching threaded wedge 88, to be inserted into the top of the U-slot. When the threaded connecting rod 74 is positioned inside the receiver 40b against the threads 86, the threaded wedge 88 is inserted on top of the rod 74 through the top of the set screw hole 89 of the set screw receiver 92 to mate with the threads of the threaded rod. 74. Then the set screw 90 is screwed into the set screw receiver 92 of the U-slot 40b against the threaded wedge 88. In this manner, the threaded wedge 88 is forced against and applies pressure to the threaded connecting rod 74, affixing it into the pedicle screw 20, but not preventing the rod 74 from being rotatable. The connecting rod 74 is then rotated to obtain the desired distance between the two pedicle screws 20 making up the pedicle screw stabilization system.

Figure 5:
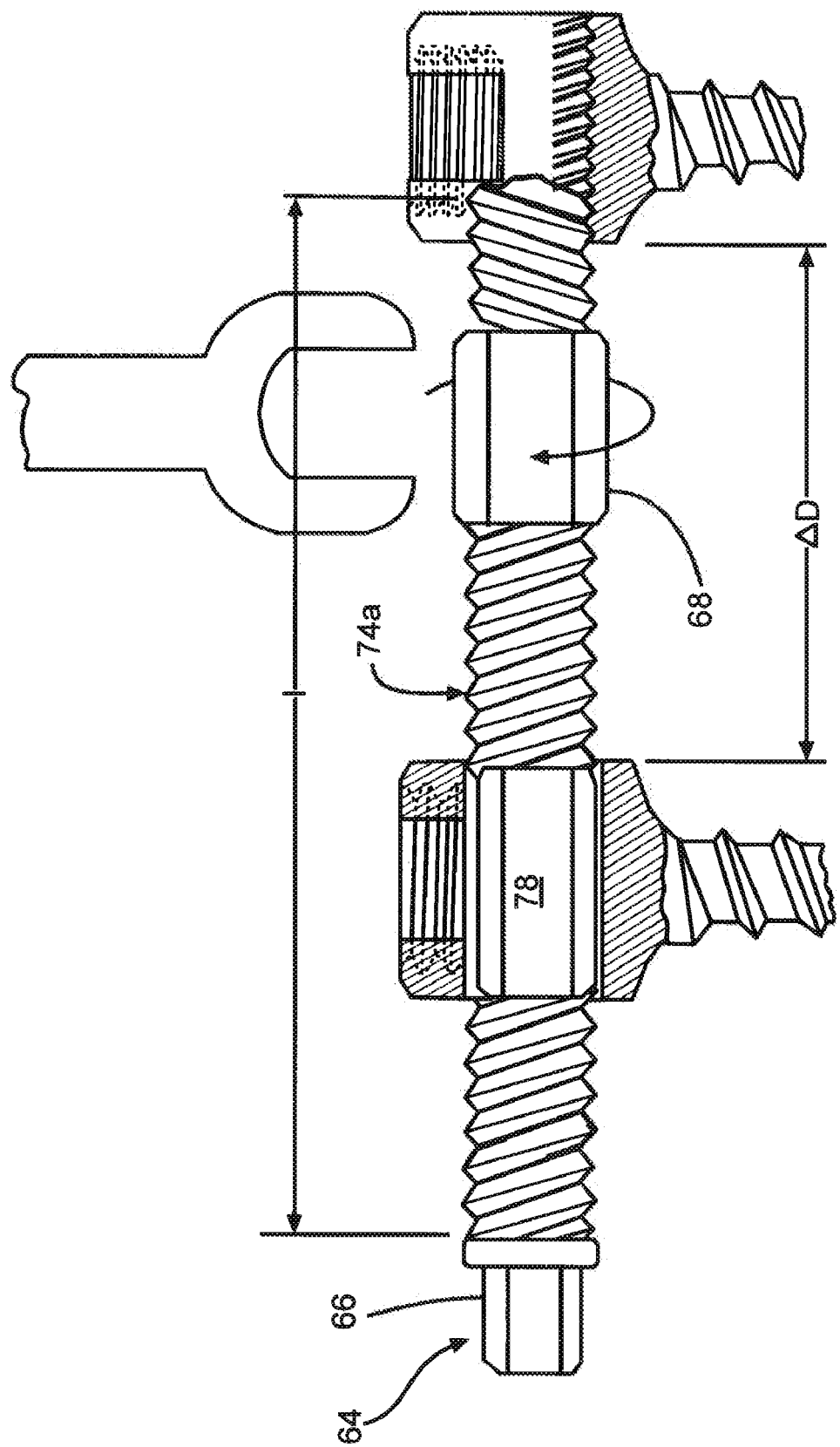
FIG. 5 is a side plan view of a threaded rod of the dynamic vertebral stabilization system illustrating different features for manually holding and rotating the rod.

FIG. 5 illustrates a portion of the length l of a threaded rod 74a, of the dynamic vertebrae stabilization system. The combination of this configuration of dynamic rod 74a with the present pedicle screws 20 forms a "turnbuckle" type mechanism which allows adjustment of the tension between at least two interconnected pedicle screws, which is a benefit, for example, where the intent is to avoid fusion of the subject vertebrae. The unshown portion of a threaded rod 74a is substantially similar to the portions shown in the figures. In the embodiment of the threaded rod 74a illustrated, the opposite ends 64 of the rod 74a are threaded in opposite directions. The threaded rod 74a of FIG. 5 illustrates different features of a threaded rod that can be used to provide alternative means for manually holding and/or rotating the threaded rod 74a to achieve the desired positional relationship between the at least two pedicle screws 20 of the system. In this embodiment, the threaded rod 74a is engageable at a rod end 64, which is has a hex-head 66 configuration, or at some position along its length l where it has a hex-nut 68 configuration in which the nut moves with the rod. It can be seen that in this configuration, turning of the hex-nut 68 causes the distance between two adjacent pedicle screws to vary, thus permitting the distance between adjacent vertebrae to be adjusted. Other configurations of the threaded rod 74 with means for manually holding and/or rotating the rod 74, which are suitable for practice in the present invention are known to and selectable by one of ordinary skill in the art.

Figure 6:
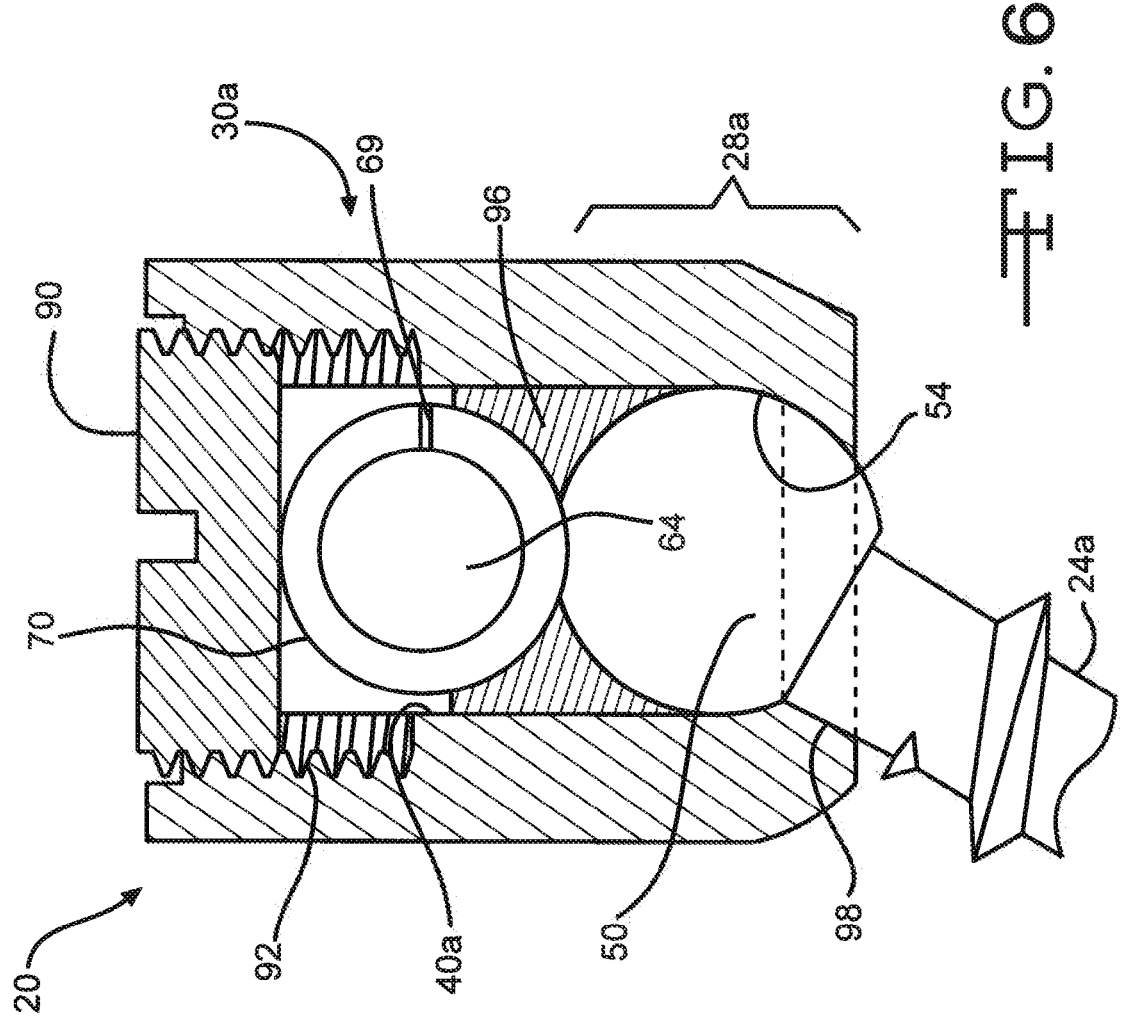
FIG. 6 is a partial cross-sectional view of the head and shank portions of a poly-axial pedicle screw of the present dynamic vertebrae stabilization system.

FIG. 6 illustrates the head and shank portions of a poly-axial type pedicle screw practicable in the present dynamic stabilization system. Such poly-axial pedicle screws are known in the field. For example, see U.S. Pat. No. 6,869,433 to Glascott, the content of which is incorporated by reference. In the example illustrated, the shank portion 28a of the pedicle screw 20 a comprises a ball and socket swivel joint, with the screw shaft 24a terminating in the ball 50 of the joint, and the bottom of the U-slot 40a being the socket 54 of the joint. The bottom of the U-slot 40a has a shaft port 98 formed therein to allow the screw shaft 24a to pass through and extend from the shank portion 28a.

A swage-like fitting 96 is formed between the ball 50 and the threaded fitting 70. The swage fitting 96 is contoured where its surfaces contact the ball 50 and the threaded fitting 70. Driving the set screw 90 against the threaded fitting 70 causes a compressive force to be exerted on the components between the set screw 90 and the socket 54. In this manner, the threaded fitting 70 is compressed against both the threaded rod 74 and the swage-like fitting 96. In turn, the ball 50 is compressed between the swage fitting 96 and the socket 54. Compression of the noted components in this manner sets up and secures their positional relationship to each other, and locks the angular position of the screw head 30a with respect to the shaft 24a. Other poly-axial pedicle screws are known to and selectable by the ordinary skilled artisan for practice in the present pedicle screw dynamic stabilization system.

In a preferred embodiment, the vertebral stabilization system utilizes a threaded polycarbonate urethane rod 74 with an outside diameter (o.d.) rd of about 4.0 mm. An anchor 70, in the form of a threaded titanium cylinder 76, is screwed onto each end 64 of the rod 74 as in FIG. 1. In this example, the cylinders 76 have an outside diameter fd of about 5.5 mm to 6.0 mm. The distance between two anchors 70 or between an anchor 70 and the corresponding rod end 64 is adjustable by threading one or both anchor 70 along the length of the rod 74.

Figure 7:
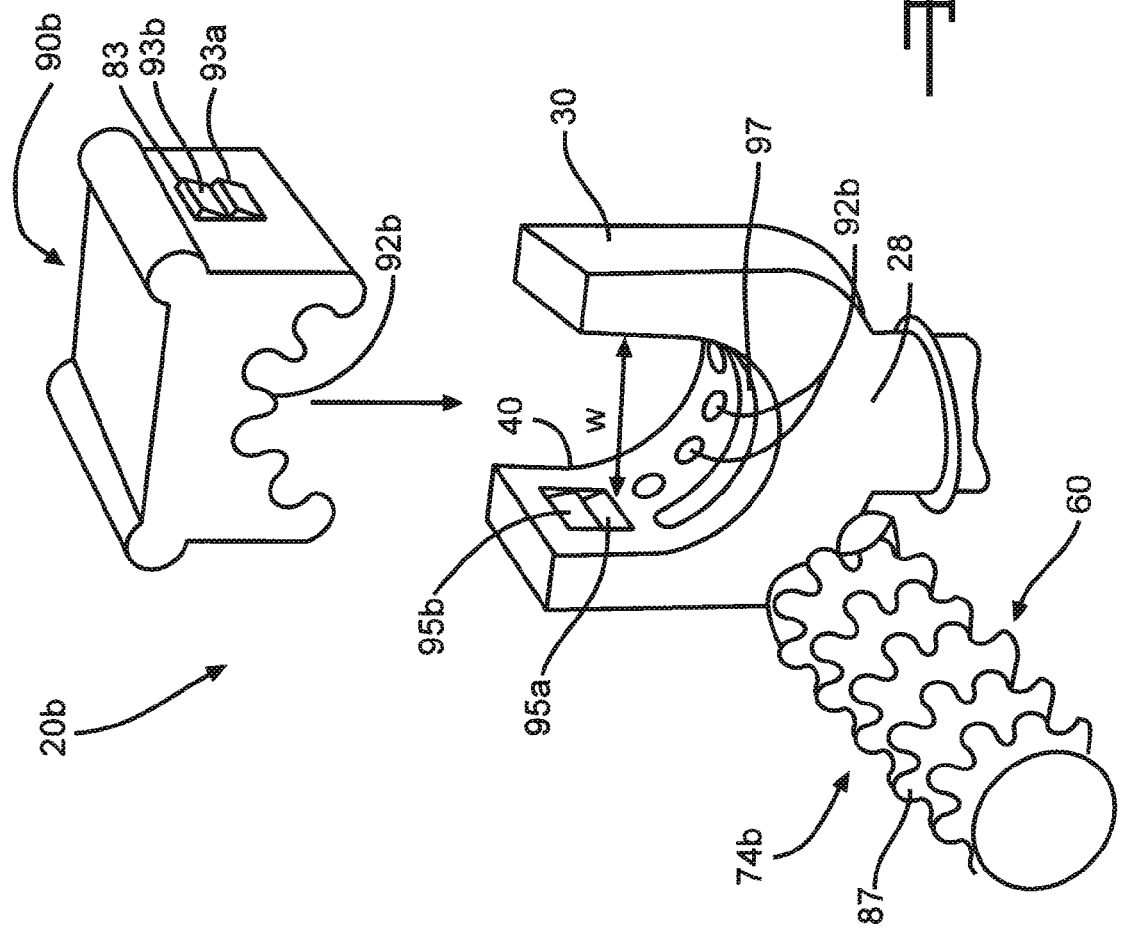
FIG. 7 is a perspective view of the head of the present dynamic vertebrae stabilization system showing an alternative embodiment wherein a rod assembly having multiple spherical protrusions is engaged with corresponding indentations in the U-slot and in the cap.

FIG. 7 is a perspective view of an alternative embodiment of the head of the present dynamic vertebrae stabilization system. In contrast to the threaded assemblies previously depicted, a rod assembly having protrusions is engaged with indentations in the U-slot and in the cap or vice versa (i.e., the indentions are in the flexible rod and the protrusions are in the anchor or U-shaped slot). Instead of a set/cap screw (FIG. 1), a snap cap 90b including at least two cap projections couples the cap to the U-slot 40.

As in the pedicle screw 20 of the previous embodiments, the pedicle screw 20b includes a head 30 with a U-slot 40 connected to a bottom shank portion 28, which makes up part of the threaded shaft 74 (not shown). The interconnecting rod assembly 60, rather than being classically threaded, includes a pimpled surface 74b, including the individual pimples being disposed in a spiraling around the rod 74b in a threaded fastener-like pattern. The inner surface of the U-slot 40 likewise includes indentations, or receiving dimples 92b, inside which the protrusions 87 of the rod assembly 60' are fitted. The dimples can be disposed in a spiraling around the rod 74b in a complementary threaded fastener-like pattern. Also, the dimples 92b can be closely juxtaposed in the spiraling pattern to form a complementary threaded fastener-like pattern, or a thread groove allowing the rod to be threadably rotated in the U-slot 40 to enable the dimple spiral to act as a thread. The inner surface of the snap cap 90b also includes indentations, or receiving dimples 92b (not shown), for accepting the protrusions 87 on the top surface of the rod assembly 60, once the cap 90b is engaged with the head 30. In FIG. 7, the protrusions 87 and indentations are spherical in shape.

In one embodiment, the protrusions 87 of the pimpled surface 74b are arranged in latitudinal rows along the surface of the rod 60. The receiving dimples 92b inside the U-slot 40 are likewise arranged in latitudinal rows. The number of rows of receiving dimples 92b depends on the size of the head 30, with more rows providing a more stable engagement between pedicle screw 20b and rod assembly 60. In another embodiment, where the protrusions 87 are arranged in latitudinal rows, the receiving dimples 92b are replaced with latitudinal grooves 97, as shown in FIG. 7. The width of the latitudinal grooves is approximately the width of the rows of protrusions 87. This embodiment has the characteristic of enabling rotational movement of the rod assembly 60 within the U-slot 40.

Figure 8:
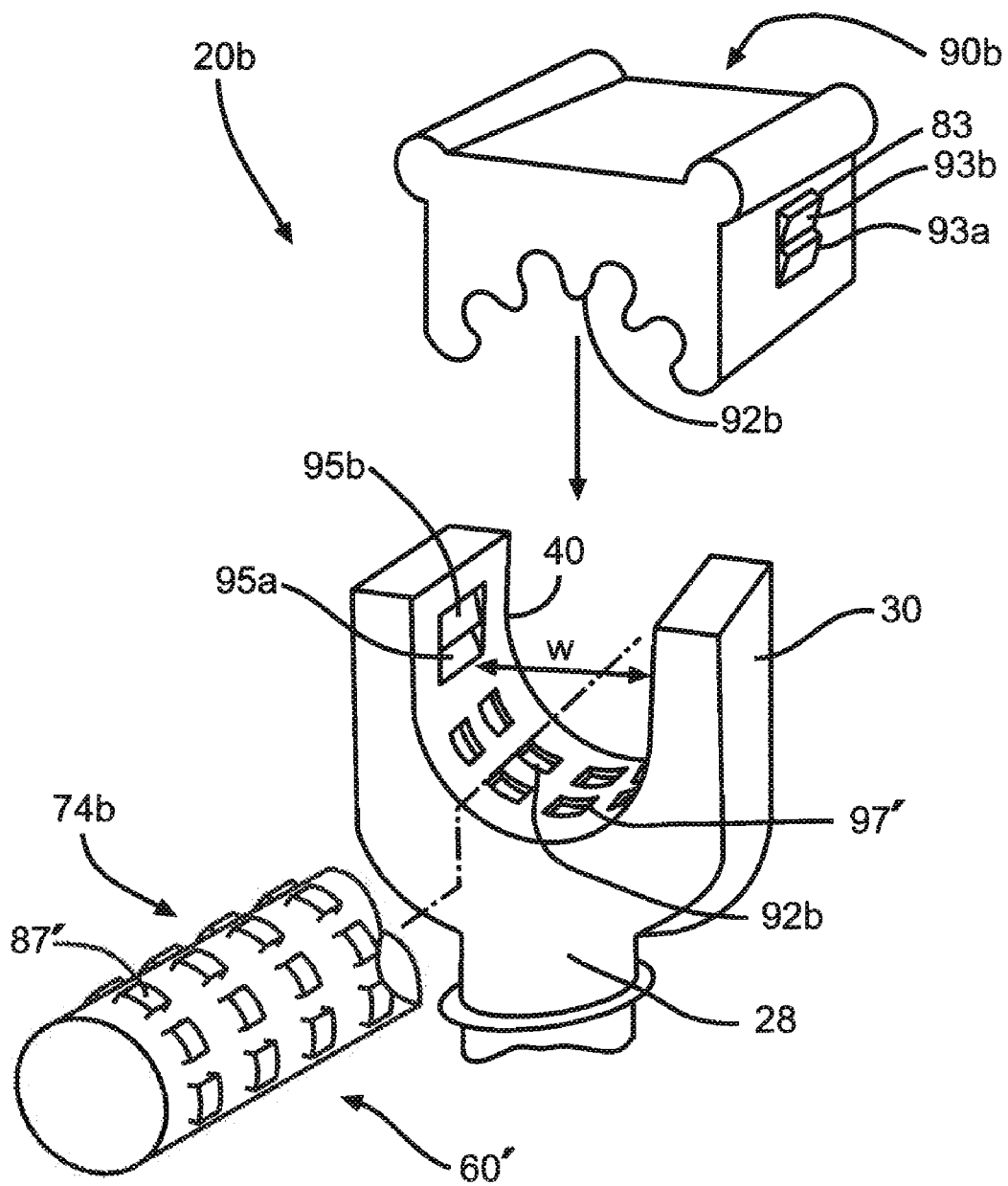
FIG. 8 is a perspective view of the head of the present dynamic vertebrae stabilization system showing a further alternative embodiment wherein a rod assembly having multiple square protrusions is engaged with corresponding indentations in the U-slot and in the cap.

Referring now to FIG. 8, in another embodiment, the protrusions 87 are formed as square raised portions 87'. Inside the U-slot 40 and the cap 90b, corresponding square recesses 92b are formed to receive the raised portions 87'. Alternatively, the same head and cap arrangement described in FIG. 7 can be used with a rod 60', wherein the square raised portions 87' fit within the groove 92b. Thus, the surgeon can choose whether to restrain the rod 60' against relative rotation between the head 30 and cap 90b, at his discretion.

In another embodiment, the protrusions 87, rather than being spherical in shape, are shaped like cubes, rods, or cylinders, with the U-slot 40 and cap 90b having cube-shaped, rod-shaped, or cylindrical receiving dimples for acceptance of the cubes, rods, or cylinders. Designers of ordinary skill in the art recognize that there are a number of possibilities for mating the rod assembly 60 with the interior of the U-slot 40 and the cap 90b. Some of the embodiments may provide more stability and/or provide a better locking mechanism than others, while some embodiments may be easier and cheaper to manufacture.

The pedicle screw 20b improves the locking of the rod assembly 60 into the head 30 of the pedicle screw. The pedicle screw 20b further protects against torsion or longitudinal sliding or slipping of the rod assembly 60 from the head 30. Instead of a set/cap screw 90 (FIG. 1), the pedicle screw 20b includes a cap 90b which includes at least two cap projections 93. The projections 93 are to be received in cap receivers 95 disposed in an inner wall of the U-slot 40. The cap 90b has a width equal to the width of the interior of the U-slot (shown as width w in FIGS. 7 and 8).

The cap projections 93 and cap projection receivers 95 are designed such that the former fit snugly into the latter, but may be any of a variety of shapes known to those of ordinary skill in the art. In the embodiment of FIGS. 7 and 8, the cap projections 93 are triangular prisms having a rectangular face 83 formed horizontally at the top, with a tapering of the prism at its bottom. Likewise, the cap receivers 95 are triangular prism-shaped recesses, for receiving the cap projections upon insertion of the cap 90b. The cap projections 93 are preferably made using a material with some elasticity, such as an elastomeric material. This ensures that, when the cap 90b is inserted into the U-slot 40, the cap projections 93 may be squeezed against the inner wall of the U-slot until they are engaged with, and fill the space of, the cap receivers 95. Once engaged, the cap projections 93 preferably fill the entirety of the cap receivers 95 and are not removable therefrom.

In connecting the rod to the pedicle screw 20b, the rod assembly 60 is slid laterally through the opening of the U-slot 40, without the cap 90b. A preferred lateral position of the rod assembly is obtained, then the rod assembly 60 is rotated until the pimples 87 fit into the dimples 92b (or grooves, cubes). The cap 90b is then disposed atop the head 30 and fit into the U-slot 40.

In the preferred embodiments shown, the first stage of the two stage anchor setting mechanism feature of the present invention is accomplished by inserting the snap cap 90b into the screw head 30 so that only the first cap projection 93a is received into a first cap projection receiver 95b. In the first stage, the snap cap 90b engages the rod 74b sufficiently tightened sufficiently to just hold the rod 74b in place in the receiver U-slot 40. At this stage, the protrusions 87 and 87' and the recesses 92b only relatively loosely engage the intervertebral rod 74b, and the intervertebral rod 74b is still rotatable/moveable within the screw head 30 and can be advanced or receded along its length l. In this configuration, the tension on the intervertebral rod 74b interconnecting two bone bridge points can be adjusted by rotating/moving the intervertebral rod 74b. The second stage of the anchor setting mechanism (74b, 90b, 92b, 95a, 95b, 93a, 93b 87, 87', 97 and 97') is accomplished by further insertion of the snap cap 90b into the screw head 30 so that the second cap projection 93b is received into the cap projection receiver 95b. The first cap projection 93a can be received into another projection receiver 95a to give greater security to the insertion of the snap cap 90b. This deeper insertion of the snap cap 90b bears on the compresses intervertebral rod 74b sufficiently to fully engage the protrusions 87 and 87' and the recesses 92b fix the position of the intervertebral rod 74b to the pedicle screw 30.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention.

What is claimed is:

1. A dynamic vertebral stabilization system, which comprises:
   a) at least two pedicle screws installable at an initial distance ΔD in adjacent vertebrae of a subject, each pedicle screw having a threaded shaft that is screwable into a vertebra segment and a pedicle screw head attached to the shaft, wherein the pedicle screw head comprises a distal set screw receiver and either an anchor receiver slot or an anchor receiving passage intermediate the threaded shaft and the set screw receiver;
   b) at least two set screws threadable into the respective set screw receivers of the at least two pedicle screws;
   c) an externally threaded connecting rod extending along an axis; and
   d) at least two anchors, each having a cross-sectional dimension that is receivable in a respective one of the anchor receiver slots or anchor receiving passages of the at least two pedicle screws, wherein each anchor has internal threads that are complementary with the threads of the connecting rod;
   e) wherein, in use, the first and second anchors are threadable onto the connecting rod in a spaced relationship of substantially the initial distance ΔD, and the connecting rod supporting the first and second anchors is receivable in the anchor receiver slots or the anchor receiving passages provided in the heads of the first and second pedicle screws having been threaded at the initial distance ΔD into adjacent vertebrae of the subject, and
   f) wherein with the first and second set screws threaded into the set screw receivers of the first and second pedicle screw heads in an untightened condition contacting the first and second anchors, the connecting rod is threadingly adjustable with respect to the anchors to thereby axially adjust the distance between the pedicie screws along the axis of the connecting rod, thus enabling fine adjustment of the initial distance ΔD to a set adjusted distance prior to further threading of the first and second set screws into a tightened condition compressing the first and second anchors into a fixed spatial relationship on the connecting rod.

2. The dynamic vertebral stabilization system of claim 1 wherein the connecting rod comprises a polycarbonate urethane composition.

3. The dynamic vertebral stabilization, system of claim 1 wherein the connecting rod has an outside diameter of at least 3.5 mm.

4. The dynamic vertebral stabilization system of claim 1 wherein the anchor receiver slot comprises a U-shaped opening between slot faces of the screw head, which opening communicates with a top surface of the screw head through the distal set screw receiver.

5. The dynamic vertebral stabilization system of claim 1 wherein the connecting rod comprises an elastomeric material.

6. The dynamic vertebral stabilization system of claim 1 wherein the connecting rod comprises means for rotating the rod.

7. The dynamic vertebral stabilization system of claim 6 wherein the connecting rod is threaded in opposite directions extending to opposed rod ends from the means for rotating the rod.

8. The dynamic vertebral stabilization system of claim 1 wherein the anchor receiving passage is a hexagonally or cubic shaped passage communicating with a top surface of the screw head through the distal set screw receiver, thereby allowing the set screw to seat into the anchor receiving passage.

9. The dynamic vertebral stabilization system of claim 1 wherein the anchors having a shape selected from the group consisting of spherical, cylindrical, polygonal, and hexagonal.

10. The dynamic vertebral stabilization system of claim 1 wherein at least one of the first and second anchors is spherical with a threaded bore that receives the threaded connecting rod and the corresponding set screw has a matching concave lower face.

11. The dynamic vertebral stabilization system of claim 1 wherein the anchors further comprise a through slot extending from an anchor outside surface to an anchor inside surface.

12. The dynamic vertebral stabilization system of claim 1 wherein the first set screw is tightenable against the first anchor in the first anchor receiver slot or in the anchor receiving passage after the first anchor is longitudinally slid.

13. A dynamic vertebral stabilization system, which comprises:
  a) at least two pedicle screws installable at an initial distance $\Delta D$ in adjacent vertebrae of a subject, each pedicle screw having a threaded shaft that is screwable into a vertebra segment and a pedicle screw head attached to the shaft, wherein the pedicle screw head comprises a distal set screw receiver and either an anchor receiver slot or an anchor receiving passage intermediate the threaded shaft and the set screw receiver;
  b) at least two set screws threadable into the respective set screw receivers of the at least two pedicle screws;
  c) a connecting rod comprising spaced apart threaded portions extending in opposite directions from an intermediate means for rotating the rod; and
  d) at least two anchors, each having a cross-sectional dimension that is receivable in a respective one of the anchor receiver slots or anchor receiving passages of the at least two pedicle screws, wherein each anchor has internal threads that are complementary with the threads of the connecting rod;
  e) wherein, in use, the first and second anchors are threadable onto the connecting rod in a spaced relationship of substantially the initial distance $\Delta D$, and the connecting rod supporting the first and second anchors is receivable in the anchor receiver slots or the anchor receiving passages provided in the heads of the first and second pedicle screws having been threaded at the initial distance $\Delta D$ into adjacent vertebrae of the subject, and
  f) wherein with the first and second set screws threaded into the set screw receivers of the first and second pedicle screw heads in an untightened condition contacting the first and second anchors, the means for rotating the rod is manipulatable to threadingly adjust the connecting rod with respect to the anchors to thereby axially adjust the distance between the pedicle screws along the axis of the connecting rod, thus enabling fine adjustment of the initial distance $\Delta D$ to a set adjusted distance prior to further threading of the first and second set screws into a tightened condition compressing the first and second anchors into a fixed spatial relationship on the connecting rod.

14. The dynamic vertebral stabilization system of claim 13 wherein the connecting rod comprises an elastomeric material.

15. The dynamic vertebral stabilization system of claim 13 wherein the anchors having a shape selected from the group consisting of spherical, cylindrical, polygonal, and hexagonal.

16. The dynamic vertebral stabilization system of claim 13 wherein the anchors further comprise a through slot extending from an anchor outside surface to an anchor inside surface.

17. A dynamic vertebral stabilization system, which comprises:
  a) at least two pedicle screws installable at an initial distance $\Delta D$ in adjacent vertebrae of a subject, each pedicle screw having a threaded shaft that is screwable into a vertebra segment and a pedicle screw head attached to the shaft, wherein the pedicle screw head comprises a distal set screw receiver and a receiver slot intermediate the threaded shaft and the set screw receiver;
  b) at least two set screws threadable into the distal set screw receivers of the at least two pedicle screws;
  c) an externally threaded connecting rod extending along an axis; and
  d) at least two threaded wedges, each having a cross-sectional dimension that is receivable in a respective one of the receiver slots of the at least two pedicle screws;
  e) wherein, in use, the wedges are receivable in the anchor receiver slots in the heads of the first and second pedicle screws, and
  f) wherein with the first and second set screws threaded into the set screw receivers of the first and second pedicle screw heads in an untightened condition contacting the first and second wedges, the connecting rod is threadingly adjustable with respect to the wedges to thereby axially adjust the distance between the pedicle screws having been threaded at the initial distance $\Delta D$ into adjacent vertebrae of the subject, thus enabling fine adjustment of the initial distance $\Delta D$ to a set adjusted distance prior to further threading of the first and second set screws into a tightened condition compressing the first and second wedges into a fixed spatial relationship on the connecting rod.

18. The dynamic vertebral stabilization system of claim 17 wherein the connecting rod comprises an elastomeric material.

19. The dynamic vertebral stabilization system of claim 17 wherein the connecting rod comprises means for rotating the rod.

20. The dynamic vertebral stabilization system of claim 19 wherein the connecting rod comprises spaced apart threaded portions extending in opposite directions from the intermediate means for rotating the rod.

* * * * *